United States Patent [19]
Arcas et al.

[11] Patent Number: 5,684,251
[45] Date of Patent: Nov. 4, 1997

[54] PORTABLE ACOUSTIC IMPEDANCE DATA ACQUISITION AND ANALYSIS SYSTEM

[75] Inventors: Noe Arcas, Plainview; Charles A. Parente, Oyster Bay; Shepard G. Kay, Merrick, all of N.Y.

[73] Assignee: Northrop Grumman Corporation, Los Angeles, Calif.

[21] Appl. No.: 412,387

[22] Filed: Mar. 28, 1995

[51] Int. Cl.$^6$ .................................................. G01N 29/04
[52] U.S. Cl. ................................................. 73/589; 73/588
[58] Field of Search ........................... 73/1 DV, 589, 73/585, 588

[56] References Cited

U.S. PATENT DOCUMENTS

| | | | |
|---|---|---|---|
| 4,079,198 | 3/1978 | Bennett | 73/585 |
| 4,601,295 | 7/1986 | Teele | 73/589 |
| 4,768,379 | 9/1988 | Arcas et al. | 73/589 |
| 5,377,546 | 1/1995 | Arcas et al. | 73/589 |

Primary Examiner—Christine K. Oda
Attorney, Agent, or Firm—Terry J. Anderson; Karl J. Hoch, Jr.

[57] ABSTRACT

A portable two microphone acoustic impedance data acquisition and analysis system provided in a lightweight, fully portable, battery powered instrument with a dual capability of either on-site or remote-site analysis of measured data on the acoustic impedance of acoustically absorbing duct liners of aircraft jet engines. The fully portable instrument is capable of being operated by relatively unskilled personnel to provide acoustic impedance and non-linearity measurements on acoustic liners at airports and aircraft maintenance facilities. The measured data on the engine duct acoustic liner can be an input directly to the data analysis system at the data acquisition site for on-site analysis, or can be recorded for input to a data analysis system at a later time, or can be recorded and transmitted, such as by a telephone modem, to a data analysis system at a remote-site. The remote-site analysis of data eliminates the requirement for skilled personnel at the aircraft to perform the relatively complex data analysis procedures.

6 Claims, 5 Drawing Sheets

FIG. 4
Data Acquisition

FIG. 7
Data Acquisition & Analysis (On-Site)

PORTABLE ACOUSTIC IMPEDANCE DATA ACQUISITION AND ANALYSIS SYSTEM

BACKGROUND OF THE INVENTION

1. Field of the Invention

The present invention relates generally to a portable acoustic impedance data acquisition and analysis system. More particularly, the subject invention pertains to a portable two microphone acoustic impedance measurement system provided in a lightweight, fully portable, battery powered instrument with a dual capability of either on-site or remote-site analysis of measured data on acoustic impedance.

The present invention provides a portable instrument for determining the acoustic impedance (acoustic resistance and acoustic reactance) of acoustically absorbing materials. More particularly, it relates to a portable instrument for determining the acoustic impedance of acoustically absorbing duct liners as are used in aircraft jet engines. The fully portable instrument is capable of being operated by relatively unskilled personnel to provide acoustic impedance and non-linearity measurements on acoustic liners at airports and aircraft maintenance facilities to ensure that noise attenuation values are maintained by acoustic liners in service, and also at acoustic liner production facilities for the purpose of monitoring quality assurance criteria.

The present invention provides for the acquisition of measured data on the acoustic impedance of an acoustic liner on-site at airports, aircraft maintenance facilities, and production facilities, and provides for either a remote or an on-site analysis of acoustical impedance data. The remote-site analysis of data on the acoustical impedance of aircraft jet engine acoustic liners eliminates the requirement for skilled personnel at the aircraft to perform the relatively complex data analysis procedures.

The present invention has applications in the aerospace industry including studies of jet engine acoustic liner designs, monitoring acoustic liner properties of acoustic liners in service in commercial and military aircraft, both in the United States and abroad. The subject invention also has civil and commercial applications in studies on, and the design of, acoustic sound absorption materials, and also on architectural acoustics for buildings, concert halls, etc.

Governmental regulatory agencies, including the ICAO and the FAA, are considering monitoring engine duct acoustic liners that are currently in service to assure that originally designed noise attenuation values are maintained in ongoing service. Moreover, NASA has adopted and set subsonic noise reduction goals, with an overall goal of developing technology to reduce the noise levels of aircraft by 10–12 EPNdB by the turn of the century. The portable two microphone system of the present invention provides a portable acoustic impedance data acquisition and analysis instrument capable of implementing noise reduction regulations by providing on-site testing of engine duct acoustic liners.

2. Discussion of the Prior Art

Arcas et al. U.S. Pat. No. 4,768,379 discloses a two microphone acoustic impedance system for measuring the steady state flow resistance of face sheets on fully assembled acoustic duct liners by subjecting the acoustic duct liner to a sinusoidal acoustic pressure field at the face sheet surface. The pressure field is applied through a cylindrical waveguide and is measured by a first pressure transducer mounted on the inside of the waveguide near the liner face and also by a second pressure transducer positioned further from the liner face. The first and second transducer measurements are combined to calculate the acoustic resistance of an assembled acoustic duct liner for the excitation frequency. If the excitation frequency coincides with the resonant frequency of the acoustic duct liner configuration, then no significant pressure will exist on the back surface of the liner face sheet. For this condition, the root mean square (RMS) pressure measured at the face sheet is equated to a static pressure drop which is used to obtain the steady state flow resistance. The RMS velocity of the oscillating pressure wave is calculated from the ratio of the RMS pressure to the acoustic resistance. A repetition of this procedure for several magnitudes of dynamic pressure permits the development of a curve for an acoustic duct liner which describes its non-linear characteristics of resistance with changes in velocity.

However, the acoustic impedance measurement system disclosed in this patent is not portable, and does not provide a dual capability of either on-site or remote-site analysis of measured data on acoustic impedance. The nonportability of the patented system does not readily provide for the acquisition of measured data on the acoustic impedance of an acoustic liner on-site at airport and aircraft maintenance facilities, or at production facilities with a remote-site analysis of acoustical impedance data. Accordingly, this system requires skilled personnel at the aircraft to perform the relatively complex data analysis procedures. Moreover, the patented system is not PC compatible, similar to the systems of the present invention.

Acoustic liners and similar structures used to attenuate noise in, for example, engine aircraft inlet and exhaust ducts, are conventionally formed of a solid backface and one or more perforate face sheets separated by a core structure. The core structure defines the distance between the backface and the face sheets without significantly affecting the acoustic properties of the liner.

Single degree of freedom sound absorptive duct liners currently in use on aircraft jet engines consist of a face sheet bonded to cellular material such as honeycomb which is itself bonded to a solid back sheet. The face sheet may consist of a perforated skin or a woven wire cloth material bonded to a perforated skin. The latter construction is currently termed a linear acoustic liner throughout the aircraft industry. The flow resistance of linear acoustic liners has shown a high degree of insensitivity to the presence of air flow along the face sheet surface of the acoustic liner similar to the flow present within engine ducts during aircraft operation.

Multiple degree of freedom acoustic liners include multiple face sheets, with the spacings between the face sheets and the solid backface being provided by multiple cores. Selected different spacings between the face sheets and the backface cause the structure to attenuate different frequencies, such that multiple frequencies of noise can be attenuated. The more face sheets or degrees of freedom possessed by the liner, the greater the range of acoustic frequencies attenuated.

The acoustic properties of an acoustic liner are greatly influenced by the face sheet resistance. The acoustic resistance of the face sheet of a linear acoustic liner is measured using conventional methods and apparatus by performing a DC (i.e., Direct Current or steady state) flow resistance measurement. The woven wire mesh side of the face sheet is subjected to a steady air flow normal to its surface. In many instances, the effect of perforate hole blockage due to the bond between the face sheet and a cellular honeycomb is incorporated by performing the measurement on the face sheet/honeycomb construction without the presence of the back sheet. The ratio of pressure drop across the face sheet to steady air flow velocity measured upstream of the face sheet determines its DC acoustic flow resistance.

A similar type of measurement can be performed on a non-linear type construction, perforated face sheet without the woven wire cloth. However, the acoustic resistance of non-linear liners has been determined to be highly influenced by the presence of grazing air flow. The acoustic resistance measured for such a construction would be indicative of its behavior only in the absence of grazing air flow.

The DC acoustic flow resistance for a given flow velocity and its variation with velocity (defined as the non-linearity) is used to insure compliance with quality assurance criteria.

SUMMARY OF THE INVENTION

Accordingly, it is a primary object of the present invention to provide a portable acoustic impedance data acquisition and analysis system. More particularly, the present invention provides a compact, lightweight and portable system for field measurements of the acoustic impedance of an engine duct acoustic liner.

A further object of the subject invention is the provision of a portable two microphone acoustic impedance measurement system provided in a lightweight, fully portable battery powered system. The portable system has a dual capability of either on-site or remote-site analysis of measured data on acoustic impedance.

The present invention provides an automated portable system for determining acoustic impedance and non-linearity capable of being operated by relatively unskilled personnel at airports, aircraft maintenance facilities, or acoustic liner production facilities for the purpose of monitoring quality assurance criteria. The fully portable system provides a detailed permanent record of all measurements performed on an acoustic liner. The portable system is capable of determining the acoustic impedance and non-linearities of an acoustic liner installed on an aircraft so as to determine any possible degradation in the acoustic attenuation properties of the acoustic liner resulting from in-service usage.

The present invention has applications in the aerospace industry including studies of jet engine acoustic liner designs, monitoring acoustic liner properties of acoustic liners in service in commercial and military aircraft, both in the United States and abroad. The subject invention also has civil and commercial applications in studies on and the design of acoustic sound absorption materials and architectural acoustics for buildings, concert halls, etc.

In accordance with the teachings herein, the present invention provides a portable acoustic impedance data acquisition and analysis system which is particularly useful in measuring the acoustic impedance of jet engine duct acoustic liners. The portable system consists of an acoustic driver which generates high intensity noise along a waveguide which is placed against the surface of the acoustic liner. Two microphones are mounted within the waveguide walls, and measure the sound field which is composed of both incident and reflected waves at the liner surface. An analysis system analyzes the measured data from the microphones and computes the acoustic impedance of the engine duct acoustic liner. The measured data from the microphones can be an input directly to the data analysis system at the data acquisition site for on-site analysis, or can be recorded for input to a data analysis system at a later time, or can be recorded and transmitted, such as by a telephone modem, to a data analysis system at a remote-site. The remote-site analysis of data eliminates the requirement for skilled personnel at the aircraft to perform the relatively complex data analysis procedures.

The portable two microphone acoustic impedance measuring system preferably utilizes a test head which weighs approximately 7–8 lbs, is designed to be hand-held for easy field usage, has an easily changeable seal, with seals with different contours being available. The test head has integral safety buttons to avoid unwanted exposure to high noise levels, and has integral software switching for remote operation, but does not contain signal conditioning for the microphones. The test head is connected to a cable which is flexible, rugged, and can have lengths up to 100'. The interface chassis weighs approximately 13 lbs, contains all electronic support for the microphones and the acoustic driver, and the power source therefor can be 115 V AC or 12 V DC. The printer weighs approximately 4.3 lbs, is portable, utilizes HP Deskjet technology, and has a parallel interface. The analyzer/controller weighs approximately 33 lbs, is portable and ruggedized, has 1 meg nonvolatile RAM with a built-in 3.5 inch disc drive.

In summary, the portable two microphone acoustic impedance measuring system features portability, with optional battery operation, a ruggedized design, broadband testing with the frequency being selectable for analysis, an automatic printout, and remote switching for remote operation, an immediate pass/fail audible detection system, easily upgradable software and hardware due to a modular design, and has user friendly, graphic interface software which reduces training time.

BRIEF DESCRIPTION OF THE DRAWINGS

The foregoing objects and advantages of the present invention for a portable acoustic impedance data acquisition and analysis system may be more readily understood by one skilled in the art with reference being had to the following detailed description of several preferred embodiments thereof, taken in conjunction with the accompanying drawings wherein like elements are designated by identical reference numerals throughout the several views, and in which.

DETAILED DESCRIPTION OF THE DRAWINGS

Figure 1:
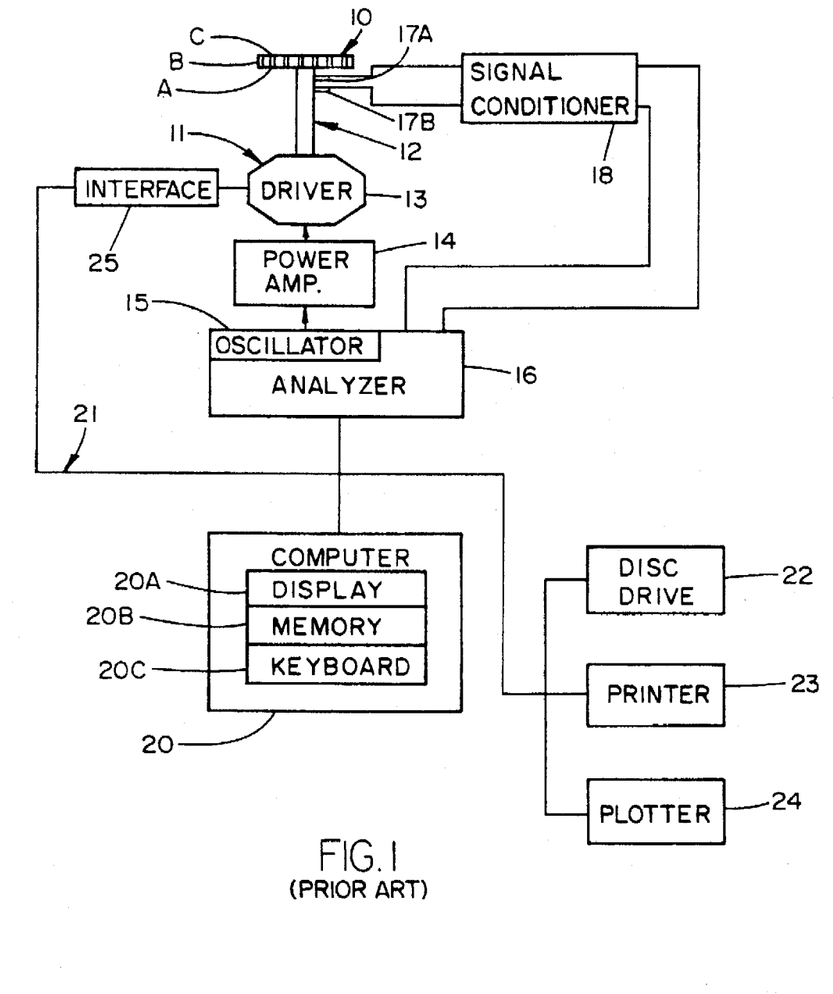
FIG. 1 is a block diagram of a prior art system for determining the acoustic impedance of an acoustic liner.

Referring to the drawings in detail, FIG. 1 is a block diagram showing the various components of a known prior art system used to determine the acoustic impedance of an aircraft jet engine acoustic liner 10. The acoustic liner 10 undergoing measurement consists of a face sheet A, a honeycomb interior B, and a back sheet C. A test head 11 which includes a waveguide 12 coupled to an acoustic signal generator 13 is positioned against the acoustic liner 10. The system is supplied with 110–120V AC, and power to the signal generator 13 is supplied by an amplifier 14 which amplifies the electrical oscillator output of a programmable oscillator 15 within a dual channel spectrum analyzer 16, thus providing an acoustic pressure field within the waveguide 12.

Two microphones 17A and 17B are mounted along the waveguide tube 12. The signal outputs of the microphones 17A and 17B are connected to a dual channel signal conditioner 18. The signal conditioner 18 provides a polarizing voltage to each of the microphones 17A and 17B and preamplifies the output signals thereof. The outputs of signal conditioner 18 are connected to the signal inputs of a dual channel spectrum analyzer 16.

A controller or microcomputer 20 is interfaced through a series of IEEE type 488 interface cables or buses 21 to a dual channel spectrum analyzer 16, a disc drive 22, a printer 23 and a plotter 24. The disc drive 22, printer 23 and plotter 24 are used for data storage, printout of test results and graphic representation of test data, respectively. The microcomputer 20 includes a display 20A and an internal memory 20B and is interfaced to a keyboard 20C.

The system of FIG. 1 may be designed for automated production testing in which the computer 20 controls the system operation, performs mathematical operations, prompts the operator by means of display 20A for data entry, and provides procedural instructions. The keyboard 20B, mounted in a slide mount, facilitates the entry of necessary information. The printer 23, also mounted on a slide mount, outputs test results in tabular formats, while the plotter 24 is used for graphic formats. The use of a printer with appropriate capability permits combining the functions of printer 23 and plotter 24. A control system interface 25 transfers control of the measurement procedure to a control panel located on the test head 11.

The test head includes a cylindrical waveguide 12 which is a tube with an inside diameter of 1.2 inches and a length of 6 inches. These dimensions are selected to allow for the highest possible sound pressure level at the open end of the waveguide 12 while assuring that the wave propagation is planar in the frequency range of interest, which is between 800 and 6000 Hz. A flexible hard rubber gasket seals the end of waveguide 12 against liner 10 even when the surface of liner 10 is moderately curved.

The two pressure transducers or microphones 17A and 17B are mounted in openings in the wall of the waveguide 12 flush with the interior wall thereof. Microphone 17A is located near the open end of waveguide 12 and thus near the liner face sheet A. Microphone 17A is positioned at a distance of 0.21 inch from the instrument liner face sheet, as measured from the instrument liner face sheet to the microphone center. This location provides an accurate reading of the sound pressure at the face sheet while assuring that the measurement is free of localized pressure disturbances caused by oscillating air masses in the immediate area of the liner face due to near field effects of holes in the face sheet. Extensive laboratory testing has demonstrated that localized pressure disturbances are no longer present at a distance of four times the dimension of openings in the face sheet. Due to the inertia of the air mass within the face sheet, the maximum in the standing wave pattern is actually shifted back away from the face sheet, so that taking measurements at this point is advantageous.

Microphone 17B, located farthest from the sample face sheet, is positioned at a location which is determined from knowledge of the resonant frequency of the liner to be tested. It should be mounted no less than 0.4 inch and no more than 1.2 inch from the center of microphone 17A. Microphone 17B should not be located at any position such that the ratio of one quarter of the test frequency wavelength to transducer center to center spacing is an integer. This criteria assures good coherence between the two pressure measurements.

Memory 20B of computer 20 stores measured test data for post-processing and allows for the transfer of calculated data to a removable floppy disc in disc drive 22 for further analysis. The spectrum analyzer 16 measures the sound pressure spectrum from each transducer and calculates a frequency response function, which is required to calculate the acoustic resistance.

Figure 2:
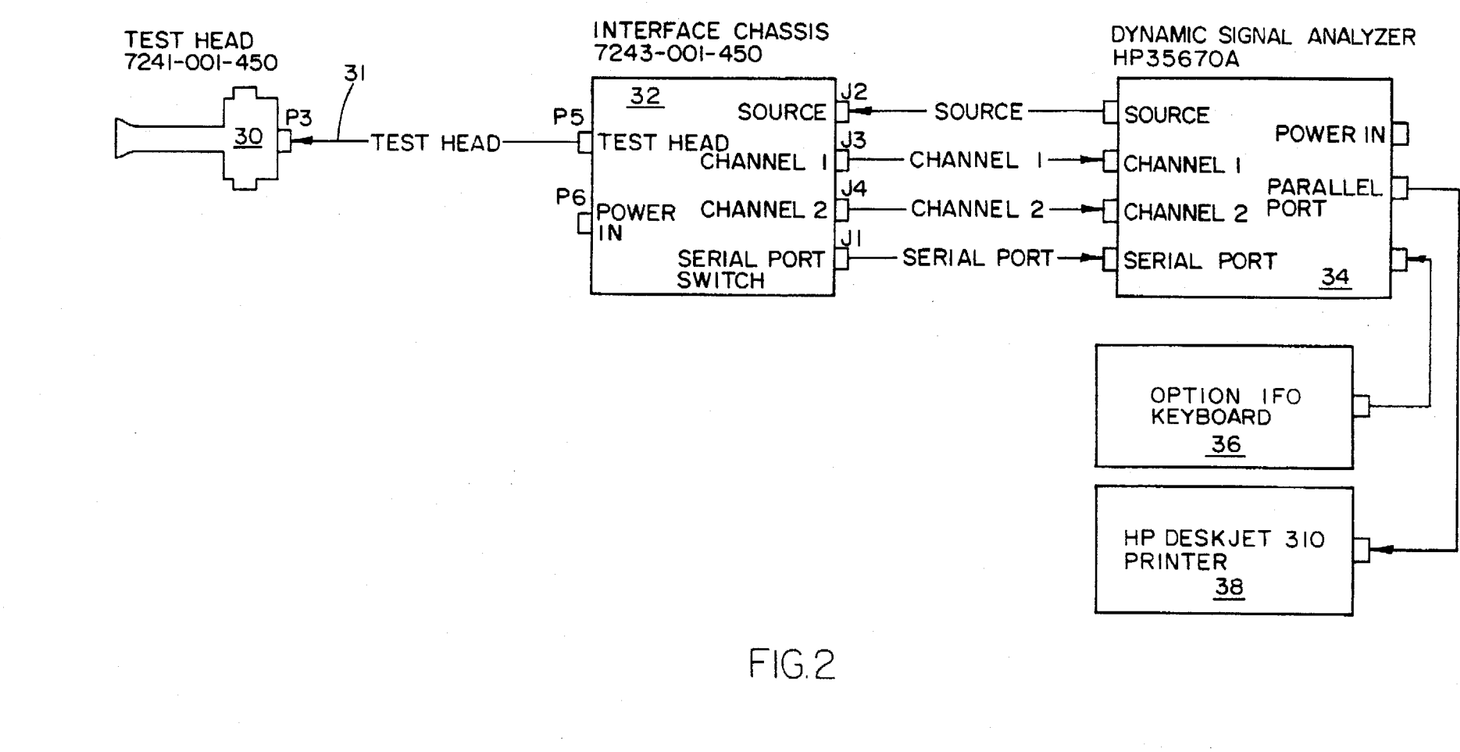
FIG. 2 is a schematic illustration of a portable acoustic impedance data acquisition and analysis system pursuant to the present invention.

FIG. 2 is a schematic block diagram of a portable acoustic impedance data acquisition and analysis system pursuant to the present invention. The system includes a test head 30, as illustrated in further detail in FIG. 3, which is coupled by an electrical cable 31 to a dual channel interface chassis 32, which in turn is coupled to a dynamic signal spectrum analyzer 34, which can be Hewlett Packard model HP35670A. The dynamic signal spectrum analyzer 34 is optionally coupled to a keyboard or analyzer keypad 36 and a printer 38, which can be Hewlett Packard model HP DESKJET 310. The test head 30, the interface chassis 32, the dynamic signal analyzer 34, the keyboard 36, and the printer 38 are powered by either 12 V DC or 115 V AC. The 12 V power supply can operate from a common 12 V automobile battery, with a possible cigarette lighter plug to connect the system thereto through an automobile cigarette lighter outlet.

Figure 3:
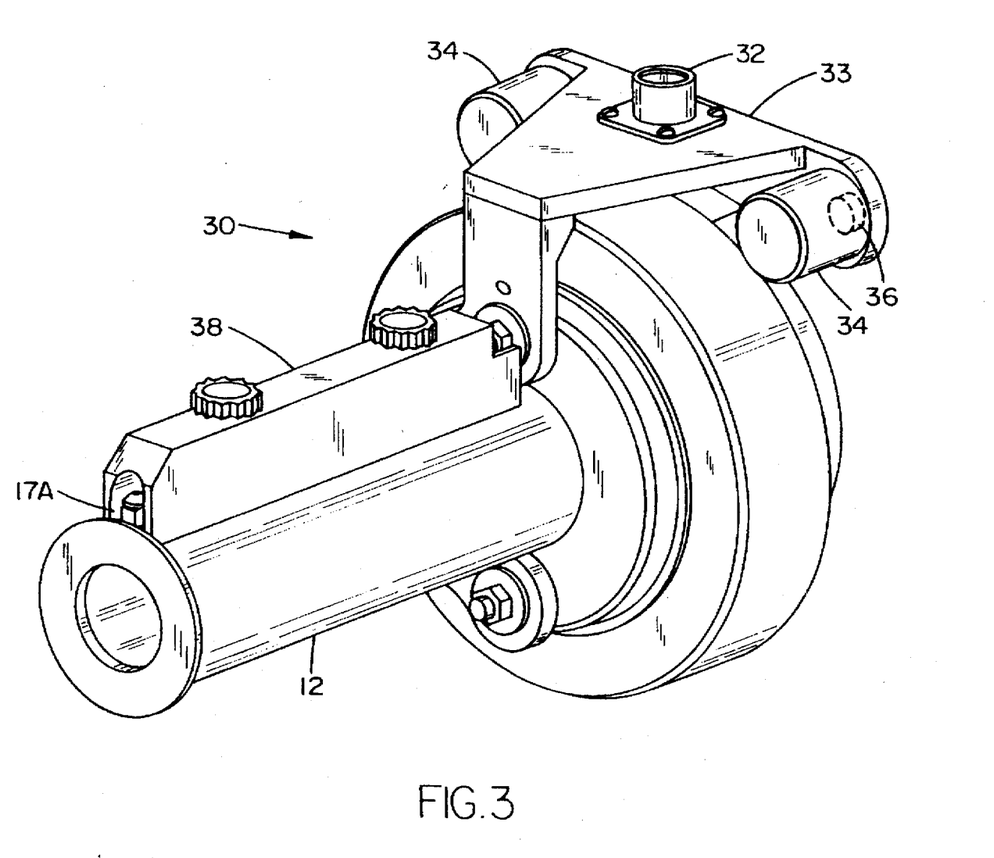
FIG. 3 is a perspective view of a portable test head used by the acoustic impedance data acquisition and analysis system of the present invention.

FIG. 3 is a perspective view of a portable test head 30 used by the acoustic impedance data acquisition and analysis system of the present invention. The test head 30 includes an electrical cable coupler socket 32, which receives a plug connector at one end of the electrical cable 31, mounted on a frame and handle 33. Two switches 34, each operated by a pushbutton 36, provide for ambidextrous operation of the portable test head. Either of the switches 34 can be pushed to operate the unit, and must be maintained depressed to continue operation. If a pushbutton 36 is released, the deactivated switch 34, which is coupled to the interface channel 32 by cable 31, will automatically deactivate operation of the test head 30 as a safety feature. The microphone 17A and 17B and the wires extending thereto are encased under a removable cover 38 for protective purposes. Overall, the portable test head 30 is much simpler, lighter, more portable, and more rugged than the test head disclosed in U.S. Pat. No. 4,768,379. The unit of FIG. 3 does not have a control panel as in the patent, the heavy frame of the patent has been eliminated, and the waveguide tube is formed of aluminum rather than brass.

Figure 4:
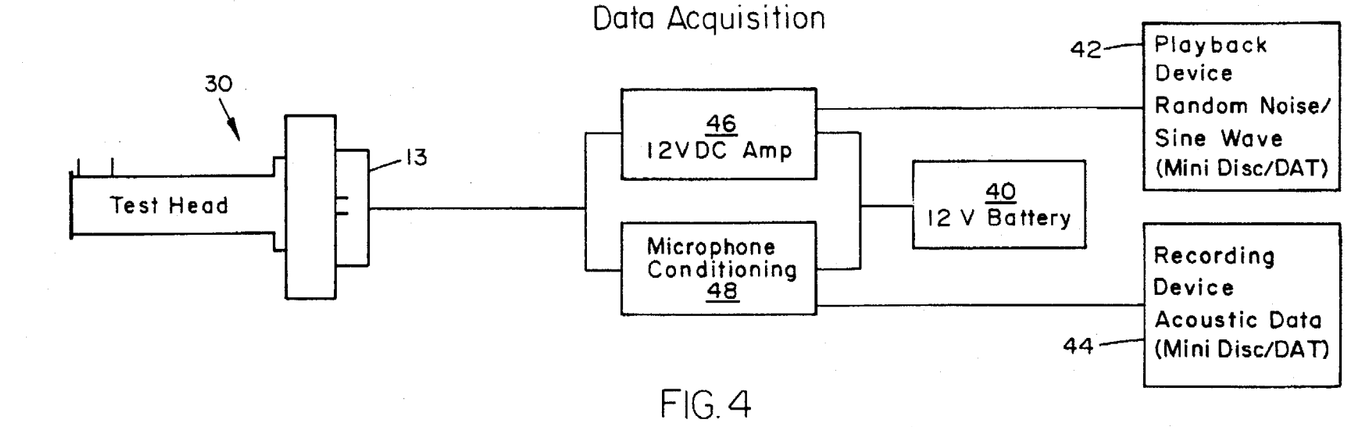
FIG. 4 illustrates a portable, battery operated, on-site acoustic impedance data acquisition system pursuant to the teachings of the present invention.

FIG. 4 illustrates a portable battery operated, on-site acoustic impedance data acquisition system pursuant to the teachings of the present invention. The portable data acquisition system includes a 12 V battery power supply 40 which provides electrical power for an audio playback source 42, an audio recorder 44, a 12 V DC power amplifier 46, and a microphone conditioning circuit 48 which supplies electrical power to the microphones 17A, 17B in the test head. The audio playback source 42 can be a digital audio tape (DAT) player, having a mini disc storage or memory, or any other suitable audio source. In this portable unit, the audio source 42 can be a source of random noise, or a sine wave at any suitable frequency. The output of the audio source 42 is amplified by power amplifier 46 to drive the acoustic generator 13 in the test head 30. The microphone conditioning circuit 48 includes a step up transformer and other appropriate DC/AC/DC circuitry to supply 18 V DC to the two microphones 17A and 17B. The outputs of the two microphones 17A and 17B proceed directly to the recorder 44, which can be a digital audio tape (DAT) recorder, recording on a mini disc format, or any other suitable audio recorder.

The data acquisition system of FIG. 4 is completely portable, and does not require any data analysis equipment, such as an interface chassis 32, or a spectral analyzer 34. Moreover, one advantage of the design of the portable system of FIG. 4, with a mini disc storage, and also the systems of FIGS. 5, 6 and 7, is that they are completely compatible with standard personal computers (PC's).

Figure 5:
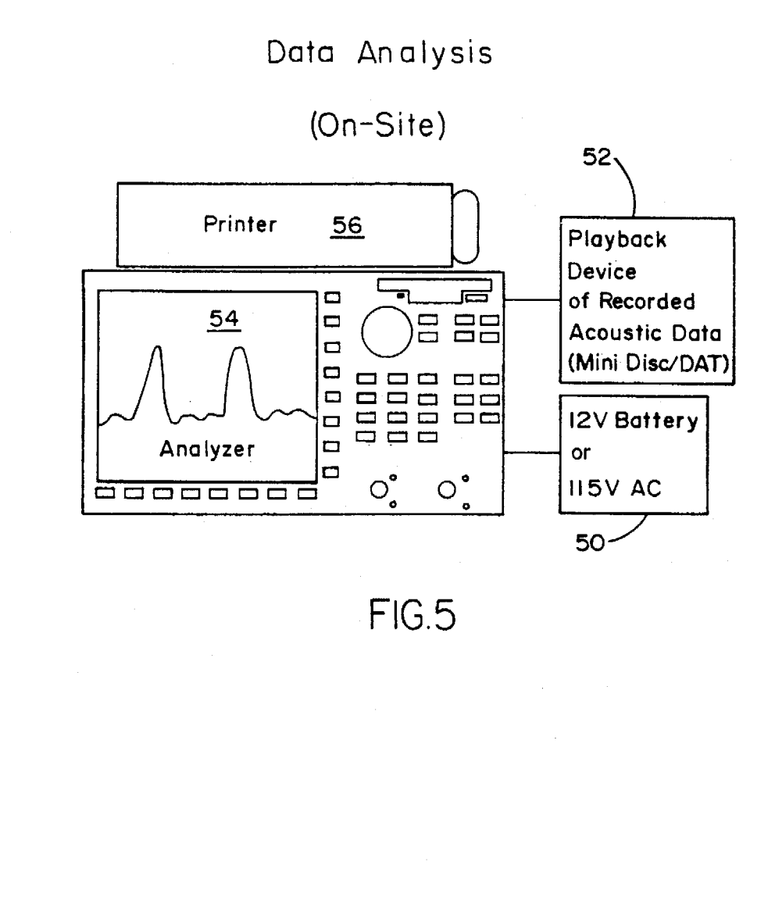
FIG. 5 illustrates a portable on-site acoustic impedance data analysis system pursuant to the subject invention.

FIG. 5 illustrates a portable on-site acoustic impedance data analysis system pursuant to the subject invention. This system includes a power supply 50, which can be a portable 12 V battery supply or 115 V AC, for supplying electrical power to an audio player 52, a spectral signal analyzer 54, and a printer 56. The audio player 52 is compatible with the audio recorder of the data acquisition system of FIG. 4, and preferably is a digital audio player with mini disc storage. The output of the audio player 52, which could have been recorded by the data acquisition system of FIG. 4, is directed to a spectral analyzer which is programmed to perform desired acoustic analyses on the recorded data, and the printer 56 prints from the spectral analyzer 54 whatever graphs or reports are requested.

Figure 6:
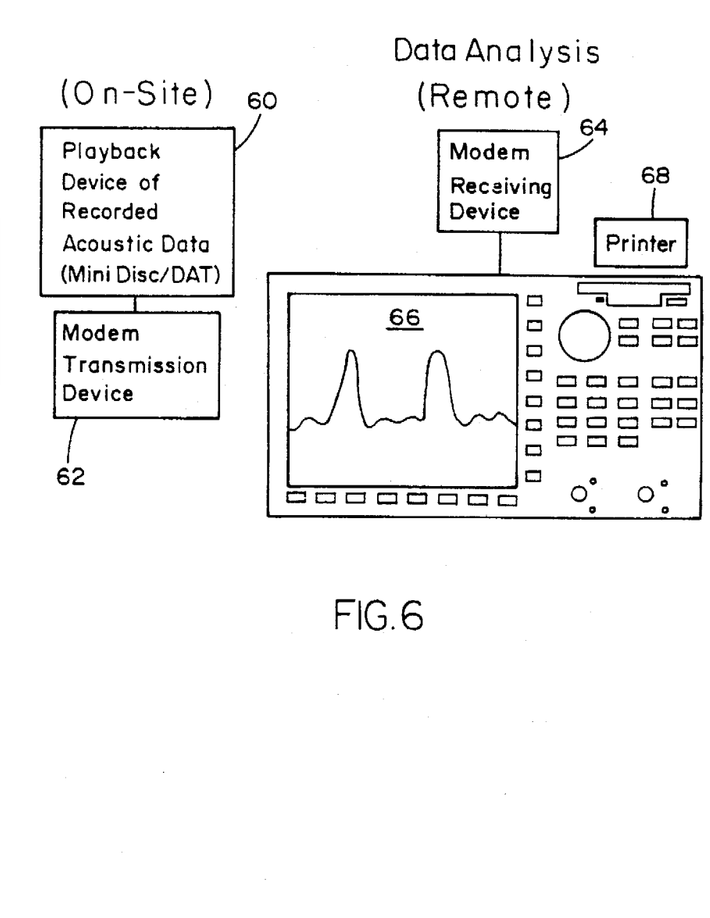
FIG. 6 depicts a block diagram of a remote acoustic impedance data analysis system pursuant to the present invention.

FIG. 6 depicts a block diagram of a remote acoustic impedance data analysis system pursuant to the present invention. In this arrangement, the output of an audio player 52, which could have been recorded by the data acquisition system of FIG. 4 and is preferably a digital audio player with mini disc storage, is transmitted via a modem 62 and a telephone connection to a remote modem receiver 64, the output of which is analyzed by a programmed spectral signal analyzer, the output of which is available from a printer 63.

Figure 7:
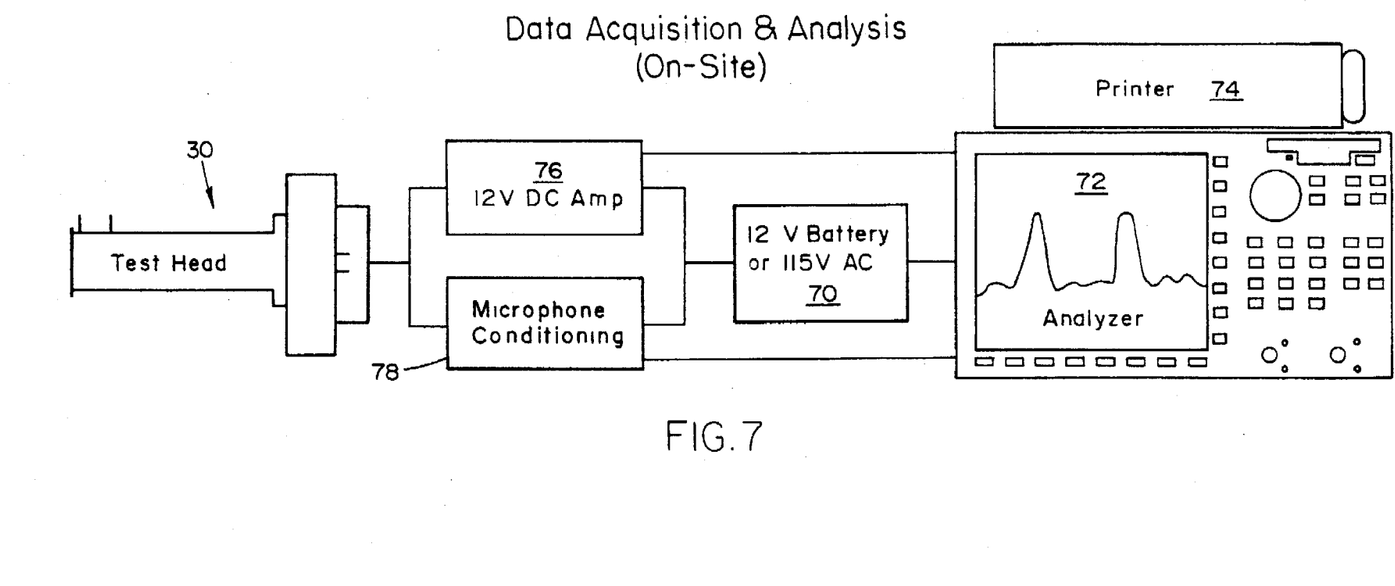
FIG. 7 is a schematic pictorial representation of a portable acoustic impedance data acquisition and data analysis system for on-site usage pursuant to the subject invention.

FIG. 7 is a schematic pictorial representation of a portable acoustic impedance data acquisition and data analysis system for on-site usage. The portable data acquisition and data analysis system includes a 12 V battery or 115 V AC power supply 70 which provides electrical power for a spectral signal analyzer 72, a printer 74, a 12 V DC power amplifier 76, and a microphone conditioning circuit 78 which supplies electrical power to the microphones 17A, 17B in the test head 30. In this portable unit, the audio test signal is supplied directly by the spectrum analyzer which is capable of supplying random noise, or a sine wave at any selected frequency. The audio output of the spectrum analyzer 72 is amplified by power amplifier 76 to drive the acoustic generator 13 in the test head 30. The microphone conditioning circuit 78 includes a step up transformer and other appropriate DC/AC/DC circuitry to supply 18 V DC to the two microphones 17A and 17B. The outputs of the two microphones 17A and 17B proceed directly to the spectral analyzer 72 for a spectral analysis thereon.

The portable two microphone acoustic impedance system has two modes of operation with two different software versions, a manual mode and an automatic mode. Both modes of operation or versions are analytically similar, but offer flexibility in performing measurements and data presentation. Data can be printed, plotted, displayed on screen, or sent to a floppy disk depending upon the analysis and software version. Both modes of operation are capable of performing both sine and broadband random testing. The general data output is frequency, sound pressure level (SPL), resistance, reactance and absorption.

Sine testing can be performed at any selected frequency for four SPL's, thus allowing investigation of non-linearity factors. Printouts of data and plots, as well as screen display of plots, are available for sine testing in both modes of operation.

Broadband testing is conducted at either of two sound pressure levels, 130 dB or 150 dB, over a frequency bandwidth of 1 KHz to 6 KHz. Printout is available listing data in increments of 24 Hz, or an abbreviated printout listing data in increments of 192 Hz. Broadband random plots are displayed on screen before printing. In both modes of operation, data can be written onto the disk, either automatically or by manual entry.

The two modes of operation differ with respect to frequency analysis. In the manual version, if this option is left to a default frequency of 0 Hz, then a broadband analysis is performed. After test completion, the software prompts asking if full data, consisting of frequencies (1 KHz to 6 KHz in 24 Hz increments), resistance and reactance, are to be sent to the floppy disk. In the automatic version, the default of 0 Hz provides operation identical to the manual version without the data to disk prompt. This version allows the operator freedom from directly interfacing with the analyzer when many measurements are conducted and data is stored on the disk in a production fashion. After each measurement is completed, the analyzer prompts for the next test point with a large illuminated square on the screen. This requires that the operator remain in the analyzer line of sight.

The portable two microphone system includes the following five basic hardware components, a spectral analyzer which can be an HP35670A spectral analyzer, a keyboard or analyzer keypad which can be HP keyboard, an interface chassis, a two microphone test head, and optionally a printer which can be an HP310 portable inkjet printer. FIG. 3 is a block diagram of the major components of the portable two microphone acoustic impedance system and the general hardware electrical interconnections thereof. An HP35670A spectral analyzer comes equipped with a built in CPU consisting of non-volatile ram disk, volatile ram disk, internal disk (PC equivalent of a floppy drive), and an interface port for an external drive. The non-volatile ram disk is equivalent to a PC hard drive, and the memory is secure after system shutdown. The volatile ram disk is equivalent to PC RAM or core memory which is lost upon system shutdown. The two software versions are stored on the non-volatile ram disk.

While several embodiments and variations of the present invention for a portable acoustic impedance data acquisition and analysis system are described in detail herein, it should be apparent that the disclosure and teachings of the present invention will suggest many alternative designs to those skilled in the art.

What is claimed is:

1. A portable acoustic impedance data acquisition and processing system comprising:

a. an audio source, comprising a digital audio tape player having a mini disc storage, for providing an audio output test signal;

b. a test head including a cylindrical waveguide having an open test end adapted to be placed against a test object, first and second pressure transducers mounted in the wall of the cylindrical waveguide flush with the interior wall thereof, with the first pressure transducer being positioned near the open end of the waveguide, and the second pressure transducer being spaced along the cylindrical waveguide from the first pressure transducer, and an acoustic signal generator for producing an acoustic signal within the cylindrical waveguide;

c. a power amplifier, coupled to the audio source, for amplifying the audio output test signal, and directing the amplified audio output signal to the acoustic signal generator of the test head;

d. an audio recorder, comprising a digital audio tape recorder having a mini disc storage, coupled to the outputs of the first and second pressure transducers, for recording the outputs of the first and second pressure transducers, whereby the portable acoustic impedance data acquisition system is completely compatible with standard personal computers;

e. a battery power supply for providing electrical power to the audio source, the first and second pressure transducers, the power amplifier, and the audio recorder, such that the data acquisition system is completely portable;

f. an audio player for playing back acoustic data signals previously recorded by the audio recorder;

g. a spectral analyzer, coupled to the audio player, which is programmed to perform desired acoustic analyses on the recorded acoustic data signals;

h. a printer, coupled to the spectral analyzer, for printing output graphs or reports as directed; and g. a modem transmitter for transmitting the output of the audio player via a telephone connection to a remote modem receiver; and the spectral analyzer is coupled to the remote modem receiver, and is programmed to perform desired acoustic analyses on the recorded acoustic data signals.

2. A portable acoustic impedance data acquisition and processing system as claimed in claim 1, wherein said audio source provides a random noise output test signal.

3. A portable acoustic impedance data acquisition and processing system as claimed in claim 1, wherein said audio source provides a sine wave at a selected frequency output test signal.

4. A portable acoustic impedance data acquisition and processing system as claimed in claim 1, wherein the test head includes left and right mounted switches, each operated by a pushbutton, which provide for ambidextrous operation of the test head, wherein a pushbutton switch is pushed to operate the test head and must be maintained depressed to continue operation, and if a pushbutton is released, the operation of the test head is automatically deactivated as a safety feature.

5. A portable acoustic impedance analysis system as claimed in claim 1, further including a DC battery power supply for supplying electrical power to the audio player, spectral analyzer, and the printer.

6. A portable acoustic impedance data acquisition and processing system as claimed in claim 1, further including a 115 VAC power supply for supplying electrical power to the audio player, spectral analyzer and the printer.

* * * * *